US010512569B2

(12) United States Patent
Carney et al.

(10) Patent No.: US 10,512,569 B2
(45) Date of Patent: Dec. 24, 2019

(54) WEARABLE ABSORBENT HYGIENE ARTICLE COMPRISING A MAGNETIC SWITCH

(71) Applicant: SCA Hygiene Products AB, Göteborg (SE)

(72) Inventors: Joshua Carney, Göteborg (SE); Yossef Schvetz, Milan (IT); Serdar Ozsumer, Milan (IT); Manuel Tramontana, Milan (IT); Alessandro Locati, Milan (IT)

(73) Assignee: ESSITY HYGIENE AND HEALTH AKTIEBOLAG, Göteborg (SE)

( * ) Notice: Subject to any disclaimer, the term of this patent is extended or adjusted under 35 U.S.C. 154(b) by 0 days.

(21) Appl. No.: 15/775,195

(22) PCT Filed: Nov. 13, 2015

(86) PCT No.: PCT/EP2015/076564
§ 371 (c)(1),
(2) Date: May 10, 2018

(87) PCT Pub. No.: WO2017/080618
PCT Pub. Date: May 18, 2017

(65) Prior Publication Data
US 2018/0369031 A1 Dec. 27, 2018

(51) Int. Cl.
*A61F 13/42* (2006.01)
*A61F 13/84* (2006.01)
(Continued)

(52) U.S. Cl.
CPC .............. *A61F 13/84* (2013.01); *A61F 13/42* (2013.01); *A61F 13/55115* (2013.01);
(Continued)

(58) Field of Classification Search
CPC .... A61F 13/42; A61F 13/55115; A61F 13/84; A61F 2013/424; A61F 2013/8479; A61F 2013/8488
See application file for complete search history.

(56) References Cited

U.S. PATENT DOCUMENTS 3,341,676 A * 9/1967 Schwarz .............. H01H 29/004
200/211
3,769,497 A * 10/1973 Frank .................. A61M 1/0021
235/94 R (Continued)

FOREIGN PATENT DOCUMENTS

| JP | S53-085958 | 7/1978 |
| RU | 2316300 C2 | 2/2008 |
| RU | 2553008 C2 | 6/2015 |

OTHER PUBLICATIONS

"Types of Magnet," https://www.thomasnet.com/articles/electrical-power-generation/magnet-types, printed May 10, 2019.*
(Continued)

*Primary Examiner* — Susan S Su
(74) *Attorney, Agent, or Firm* — Drinker Biddle & Reath LLP

(57) ABSTRACT

A wearable absorbent hygiene article includes an electronics unit, a power source and a magnetic switch. The magnetic switch operably couples the electronics unit to the power source. The magnetic switch is configured such that the power source supplies power to the electronics unit when the magnetic switch is in an ON state and such that the power source does not supply power to the electronics unit when the magnetic switch is in an OFF state. The magnetic switch is further configured such that a movement of a magnet relative to the magnetic switch switches the magnetic switch from the OFF state to the ON state.

22 Claims, 14 Drawing Sheets

(51) Int. Cl.
    *H01H 36/00*        (2006.01)
    *A61F 13/551*       (2006.01)
(52) U.S. Cl.
    CPC ........ *H01H 36/00* (2013.01); *H01H 36/0006*
               (2013.01); *A61F 2013/424* (2013.01); *A61F*
                    *2013/8479* (2013.01); *A61F 2013/8488*
                                                    (2013.01)

(56) References Cited

U.S. PATENT DOCUMENTS

| | | | |
|---|---|---|---|
| 6,477,410 B1* | 11/2002 | Henley ................ | A61N 1/0428 601/1 |
| 2004/0019400 A1 | 1/2004 | Popp et al. | |
| 2004/0113801 A1 | 6/2004 | Gustafson et al. | |
| 2004/0178807 A1* | 9/2004 | Sahlberg ................ | A61F 13/42 324/694 |
| 2005/0033250 A1 | 2/2005 | Collette et al. | |
| 2006/0266104 A1 | 11/2006 | Gordon | |
| 2007/0252711 A1* | 11/2007 | Long ................ | A61F 13/42 340/573.5 |
| 2008/0033383 A1* | 2/2008 | Cantor ................ | A61F 13/42 604/361 |
| 2009/0163111 A1* | 6/2009 | Garbos ................ | A63H 3/28 446/298 |
| 2010/0056963 A1 | 3/2010 | Shaviv | |
| 2011/0095884 A1* | 4/2011 | Xu ................ | A61F 13/42 340/539.11 |
| 2011/0140885 A1* | 6/2011 | Hummer ................ | G08B 21/12 340/539.13 |
| 2011/0140903 A1 | 6/2011 | Collins et al. | |
| 2012/0172824 A1 | 7/2012 | Khaknazarov et al. | |
| 2015/0320609 A1* | 11/2015 | Thoen ................ | A61F 13/42 340/573.5 |
| 2016/0250081 A1* | 9/2016 | Pugh ................ | G08B 21/245 604/361 |
| 2018/0353355 A1 | 12/2018 | Carney et al. | |

OTHER PUBLICATIONS

European Office Action dated Mar. 4, 2019 issued in European patent application No. 15 795 152.6.
Russian Office Action dated Jan. 10, 2019 issued in Russian patent application No. 2018121031(6 pages) and its partial English-language translation thereof (2 pages).
Office Action dated May 15, 2019 issued in U.S. Appl. No. 15/775,075 with double-patenting rejection on p. 3.
Decision to Grant dated Jun. 11, 2019 issued in Russian patent application No. 2018121039 (13 pages) and its English-language translation thereof (8 pages).
Decision to Grant dated Jun. 11, 2019 issued in Russian patent application No. 2018121031 (11 pages) and its English-language translation thereof (6 pages).
Japanese Office Action dated Aug. 9, 2019 issued in Japanese patent application No. 2018-524360 (5 pages) and its English-language translation thereof (5 pages).
Japanese Office Action dated Aug. 9, 2019 issued in Japanese patent application No. 2018-524365 (4 pages) and its English-language translation thereof (5 pages).

* cited by examiner

WEARABLE ABSORBENT HYGIENE ARTICLE COMPRISING A MAGNETIC SWITCH

CROSS-REFERENCE TO PRIOR APPLICATION

This application is a § 371 National Stage Application of PCT International Application No. PCT/EP2015/076564 filed Nov. 13, 2015, which is incorporated herein in its entirety.

TECHNICAL FIELD

The present disclosure relates to a wearable absorbent hygiene article, and particularly to a wearable absorbent hygiene article with an electronics unit and a power source. The present disclosure also relates to methods of using the wearable absorbent hygiene article.

BACKGROUND

Typically, a separate external attachable logging unit may be used to monitor the conditions of a wearable absorbent hygiene article. Typically, the wearable absorbent hygiene article is sold and packaged separately from the logging unit, and, therefore, the user must attach the logging unit to the wearable absorbent hygiene article before using the wearable absorbent hygiene article. The logging unit is typically attachable to the outside surface of the wearable absorbent hygiene article. Furthermore, the logging unit may be of a substantial size.

However, with such systems, use of the system typically includes additional complicated steps in addition to the steps required to use a conventional wearable absorbent hygiene article.

An electronics unit and a power source, such as a cell, may be included in a wearable absorbent hygiene article. The electronics unit may include sensors which monitor, and optionally transmit, the conditions of the wearable absorbent hygiene article such as the wetness. Such electronics units may include a wetness sensor and/or a transmitter and/or a receiver. The electronics unit may be powered by the power source. With such a configuration, the power source may start powering the electronics unit after manufacturing/packaging of the wearable absorbent hygiene article. Accordingly, the power source will power the electronics unit for the duration from the completion of manufacturing/packaging to just prior to use. During this time, the wearable absorbent hygiene article and the electronics unit are not being used, and, therefore, the energy in the power source is being wasted. Subsequently, when the wearable absorbent hygiene article is put to use, a large portion of the capacity of the power source may already be depleted, and, therefore, the electronics unit may have a limited period in which it may be powered by the power source. The duration in which the wearable absorbent hygiene article is not being used can vary considerably, and may range from a few months to a few years. During this time, the wearable absorbent hygiene article may be transported and stored for long periods of time. Depending on the size of the power source and when the wearable absorbent hygiene article is finally put to use, it may be that the power source does not have any stored energy remaining in it.

A user of such wearable absorbent hygiene articles may have to use many wearable absorbent hygiene articles over a period of time. Accordingly, it is desirable that the use of the wearable absorbent hygiene article does not involve any complicated steps.

With recent developments of low-cost, environmentally-friendly, low profile, disposable power sources, such as disposable cells, and semiconductor chips, a wearable absorbent hygiene article may be provided with the cell and/or at least a portion of the electronics unit disposed between two layers of the wearable absorbent hygiene article. With such wearable absorbent hygiene articles, the power source and/or at least a portion of the electronics unit may be integrated within the wearable absorbent hygiene article such that access to the power source and/or the electronics unit is limited or not possible.

In view of the above, there is a need for an improved convenient-to-use wearable absorbent hygiene article in which an electronics unit may be powered for a longer period of time when the wearable absorbent hygiene article is in use. There is also a need for improved methods of using the wearable absorbent hygiene article.

SUMMARY

Accordingly, it is desired to provide an improved convenient-to-use wearable absorbent hygiene article in which an electronics unit may be powered for a longer period of time when the wearable absorbent hygiene article is in use. It is also desired to provide an improved method of using the wearable absorbent hygiene article.

According to a first aspect, there is provided a wearable absorbent hygiene article. The wearable absorbent hygiene article includes an electronics unit, a power source and a magnetic switch. The magnetic switch operably couples the electronics unit to the power source. The magnetic switch is configured such that the power source supplies power to the electronics unit when the magnetic switch is in an ON state and such that the power source does not supply power to the electronics unit when the magnetic switch is in an OFF state. The magnetic switch is configured such that a change in a magnetic field experienced by the magnetic switch switches the magnetic switch from the OFF state to the ON state.

Throughout this disclosure, the term 'wearable absorbent hygiene article' is to be interpreted as any article that can be worn by a user and which may absorb certain substances expelled by the user. Wearable absorbent hygiene articles include pull-on diapers; refastenable diapers; reusable diapers; and other types of diapers.

For example, the wearable absorbent article may include: a liquid permeable top layer adapted to face the wearer during use and adapted to allow a fluid such as urine or other bodily fluids to pass through; a liquid impermeable back layer adapted to face away from the wearer and adapted to prevent the fluid from passing through; and an absorbent member located between the top layer and the back layer.

Throughout this disclosure, the term 'electronics unit' refers to any unit which includes electronic components and which requires electrical power to perform its intended function.

Throughout this disclosure, the term 'magnetic switch' refers to any switch which is configured to be in a particular state depending on the magnetic field experienced by the switch. The magnetic switch may switch between states when the magnetic field experienced by the magnetic switch changes. The particular change in magnetic field required to switch the magnetic switch between states may be predetermined depending on the particular configuration of the magnetic switch.

Throughout this disclosure, the term 'power source' refers to any device which is capable of storing energy for a period of time. The power source may supply electrical power.

When the magnetic switch is in an ON state, the power source supplies power to the electronics unit such that the electronics unit may perform its intended function. When the magnetic switch is in an OFF state, the power source does not supply power to the electronics unit such that the electronics unit cannot perform its intended function. When the magnetic switch is in the OFF state, the power source largely maintains its stored energy.

A change in a magnetic field experienced by the magnetic switch switches the magnetic switch from the OFF state to the ON state. The change in a magnetic field experienced by the magnetic switch required to switch the magnetic switch may be a predetermined change or a set of predetermined changes in a magnetic field experienced by the magnetic switch. Optionally, the magnetic switch is configured to permanently switch such that the magnetic switch cannot be switched from the ON state to the OFF state. Or, optionally, another change in a magnetic field experienced by the magnetic switch may switch the magnetic switch from the ON state to the OFF state.

Typically, during use of the wearable absorbent hygiene article, the article is handled and manipulated by the user. With such a configuration, during this manipulation, a change in a magnetic field experienced by the magnetic switch may occur, thereby causing the magnetic switch to switch from the OFF state to the ON state.

Hence, with such a configuration, it is possible to provide a convenient-to-use wearable absorbent hygiene article in which an electronics unit may be powered for a longer period of time when the wearable absorbent hygiene article is in use.

In one embodiment, the magnetic switch is a reed switch.

With such a configuration, the magnetic switch can be embedded in the wearable absorbent hygiene article such that it does not cause substantial discomfort to the user. Also, with such a configuration, the magnetic switch is sealed from any substances expelled by the user.

In one embodiment, the magnetic switch is configured such that a movement of a switching element relative to the magnetic switch switches the magnetic switch from the OFF state to the ON state.

Throughout this disclosure, the term 'switching element' refers to any device/material which is capable of creating/altering a magnetic field.

The switching element is an element which is suitable for switching the magnetic switch from the OFF state to the ON state.

The movement of the switching element results in the change in the magnetic field experienced by the magnetic switch.

For example, the switching element may create its own magnetic field, and, therefore, the movement of the switching element may result in the change in the magnetic field experienced by the magnetic switch.

For example, the switching element may alter an existing magnetic field, and, therefore, the movement of the switching element may result in the change in the magnetic field experienced by the magnetic switch.

'A movement of a switching element relative to the magnetic switch' refers to 'a relative movement between a switching element and the magnetic switch'.

A movement of a switching element relative to the magnetic switch switches the magnetic switch from the OFF state to the ON state. The movement of the switching element relative to the magnetic switch required to switch the magnetic switch may be a predetermined movement or a set of predetermined movements. Optionally, the magnetic switch is configured to permanently switch such that the magnetic switch cannot be switched from the ON state to the OFF state. Or, optionally, another movement of the switching element or another switching element, relative to the magnetic switch may switch the magnetic switch from the ON state to the OFF state.

Typically, during use of the wearable absorbent hygiene article, the article is handled and manipulated by the user. With such a configuration, during this manipulation, a switching element may be moved relative to the magnetic switch, thereby causing the magnetic switch to switch from the OFF state to the ON state.

In one embodiment, the wearable absorbent hygiene article further includes the switching element.

Typically, during use of the wearable absorbent hygiene article, the article is unpackaged from a packaging; and/or unfolded from a folded configuration; and/or applied to a user. With the above configuration, in the unpacking/unfolding/applying steps a switching element may be moved relative to the magnetic switch thereby causing the magnetic switch to switch from the OFF state to the ON state.

Ideally, the use of a wearable absorbent hygiene article with an electronics unit should involve the same steps as the use of a typical wearable absorbent hygiene article—any additional steps in using a wearable absorbent hygiene article with an electronics unit may detract from the convenience of using the product. With this configuration, it is possible to automatically start powering the electronics unit in one of the unpacking/unfolding/applying steps, without requiring any additional steps from the user.

Hence, with such a configuration, it is possible to provide a convenient-to-use wearable absorbent hygiene article in which an electronics unit may be powered for a longer period of time when the wearable absorbent hygiene article is in use.

In one embodiment, the wearable absorbent hygiene article includes a first region and a second region. The magnetic switch is disposed in the first region and the switching element is disposed in the second region or the switching element is disposed in the first region and the magnetic switch is disposed in the second region.

The first region and/or the second region may be panel regions of the wearable absorbent hygiene article.

Throughout this disclosure, the term 'panel region' refers to an area of a panel of the wearable absorbent hygiene article. Such 'panel regions' refer to the whole region of the panel including the corresponding regions of the various layers of the wearable absorbent hygiene article.

With such configurations, a movement of the first region relative to the second region may cause the magnetic switch to switch from the OFF state to the ON state. A movement of a first region relative to a second region typically occurs during unpacking/unfolding/application of the wearable absorbent hygiene article. Accordingly, with such a configuration, no extra steps are required to start powering the electronics unit. Hence, with such a configuration, the magnetic switch would automatically switch from the OFF state to the ON state during unpacking/unfolding/application of the wearable absorbent hygiene article.

In one embodiment, the wearable absorbent hygiene article includes a main portion. The first region is one region of the main portion. The second region is another region of the main portion.

With such a configuration, a movement of one region of the main portion relative to another region the main portion may cause the magnetic switch to switch from the OFF state to the ON state. A movement of one region of the main portion relative to another region of the main portion typically occurs during unpacking/unfolding/application of the wearable absorbent hygiene article. Accordingly, with such a configuration, no extra steps are required to start powering the electronics unit. Hence, with such a configuration, the magnetic switch would automatically switch from the OFF state to the ON state during unpacking/unfolding/application of the wearable absorbent hygiene article. Moreover, typically, the main portion is the most padded area and, therefore, with such a configuration, the magnetic switch and the switching element may not cause substantial discomfort to the user. Also, as the electronics unit is typically provided for in the main region, such a configuration allows for a simple arrangement as the magnetic switch and the switching element are disposed relatively close to the electronics unit.

In one embodiment, the wearable absorbent hygiene article is in a folded configuration where the wearable absorbent hygiene article is folded such that the first region and the second region at least partially overlap. In a particular embodiment, the main portion is folded.

Typically, in a folded configuration at least two areas of the wearable absorbent hygiene article will overlap. Accordingly, with such a configuration, upon unfolding the wearable absorbent hygiene article, which may be an essential step in the application of the wearable absorbent hygiene article, the magnetic switch would automatically switch from the OFF state to the ON state. This provides for a reliable switching.

In one embodiment, the wearable absorbent hygiene article is in a contracted configuration where the main portion is contracted such that the first region and the second region are in closer proximity to each other than in an expanded configuration of the wearable absorbent hygiene article.

In the contracted configuration the main portion may be contracted along a length of the main portion. As expanding the contracted main portion may be an essential step in the application of the wearable absorbent hygiene article, the magnetic switch would automatically switch from the OFF state to the ON state. This provides for a reliable switching.

In one embodiment, the first region and the second region are releasably attachable to each other.

With such a configuration, attaching the first region to the second region may cause the magnetic switch to switch from the OFF state to the ON state. An attachment of one region to another region typically occurs during application of the wearable absorbent hygiene article. Accordingly, with such a configuration, no extra steps are required to start powering the electronics unit. Hence, with such a configuration, the magnetic switch would automatically switch from the OFF state to the ON state during the application of the wearable absorbent hygiene article. Moreover, as attaching a first region to a second region may be an essential step in the application of the wearable absorbent hygiene article, the magnetic switch would automatically switch from the OFF state to the ON state. This provides for a reliable switching.

In one embodiment, the magnetic switch is configured such that attaching the first region and the second region to each other switches the magnetic switch from the OFF state to the ON state.

In one embodiment, at least one of the first region and the second region is a side flap or a belt flap.

In one embodiment, the first region is a main portion and the second region is a side portion of the wearable absorbent hygiene article.

Typically, during unpacking/unfolding/application of the wearable absorbent hygiene article, a side portion and a main portion of the wearable absorbent hygiene article experience the greatest degree of relative movement. Accordingly, with such a configuration, the magnetic switch may experience a large change in magnetic field. Hence, with such a configuration, more reliable switching may be possible.

In one embodiment, the wearable absorbent hygiene article is in a folded configuration where the wearable absorbent hygiene article is folded such that the main portion and the side portion at least partially overlap.

With such a configuration, to allow application of the wearable absorbent hygiene article to a wearer, it is ensured that during unfolding, the user must effect a relative movement between the side portion and the main portion of the wearable absorbent hygiene article. Accordingly, this may provide for reliable switching.

In one embodiment, the magnetic switch is configured such that a bending and/or stretching and/or compressing of a portion of the wearable absorbent hygiene article switches the magnetic switch from the OFF state to the ON state. In a particular embodiment, the portion is a main portion of the wearable absorbent hygiene article.

With such configurations, as a bending and/or stretching and/or compressing of a portion of the wearable absorbent hygiene article typically occurs during unpacking/unfolding/application of the wearable absorbent hygiene article, it may be possible to ensure reliable switching.

In one embodiment, the electronics unit includes at least one sensor for sensing a physical environment presence in the wearable absorbent hygiene article. The at least one sensor may be a wetness sensor and/or a temperature sensor and/or a chemical sensor and/or a biological sensor.

The wetness sensor may be configured to detect the presence and/or level of a liquid. The temperature sensor may be configured to detect the temperature present. The chemical sensor may be configured to detect one or more chemicals. The biological sensor may be configured to detect biological matter such as bacteria present in urine.

In one embodiment, the electronics unit includes a transmitter and/or a receiver.

In one embodiment, the power source is a cell. In a particular embodiment, the power source is a paper cell.

With such configurations, the power source may form a low profile which may reduce the discomfort caused to the user.

In one embodiment, the wearable absorbent hygiene article includes a liquid permeable top layer; a back layer; and an absorbent member. The liquid permeable top layer is adapted to face the wearer during use. The back layer is opposite to the top layer. The absorbent member is located between the top layer and the back layer. At least one, and, in particular embodiments, all of the power source, the magnetic switch and at least a portion of the electronics unit are disposed between the top layer and the back layer.

It is envisaged that any sensors, parts of such sensors, or components connecting the sensors with other components of the electronics unit, may be disposed on an outer surface of the absorbent article, such as on the wearer-facing side of the top layer, or on the outer surface of the back layer. For example, chemical sensors, such as gas sensors, may be positioned on the outer surface of the back layer to provide indications of a fecal discharge event; biological sensors, such as for detecting presence of bacteria in urine, may be positioned on the wearer-facing side of the top layer, while conducting leads, connecting such sensors to other components of the electronics unit may be disposed between the top layer and the back layer. Also, a wetness sensor may be disposed between the top layer and the back layer, while conducting leads, connecting such sensors to other components of the electronics unit may be disposed on the outer surface of the back layer. It is also envisaged that the complete electronics unit is disposed between the top layer and the back layer.

The top layer and the back layer may not be the only layers of the of the wearable absorbent hygiene article. Rather, further layers may be provided between the top layer and the back layer. Such further layers will be known to the person skilled in the art.

The absorbent member may be located anywhere between the top layer and the back layer.

With such configurations, the power source, the magnetic switch and/or the electronics unit do not cause substantial discomfort to the user. Moreover, attaching a separate logging unit to the wearable absorbent hygiene article is not required as the sensing capabilities are already embedded in the wearable absorbent hygiene article.

In one embodiment, the switching element is disposed between the top layer and the back layer.

With such a configuration, a separate entity containing a switching element is not required to switch the magnetic switch from the OFF state to the ON state. Accordingly, a manipulation of the wearable absorbent hygiene article itself may cause the magnetic switch to switch from the OFF state to the ON state.

In one embodiment, the switching element includes a magnet.

Throughout this disclosure, the term 'magnet' refers to any device/material which creates a magnetic field.

In one embodiment, the switching element includes a ferromagnetic material. In one embodiment, the switching element includes a ferrimagnetic material. In one embodiment, the switching element includes a paramagnetic material. In one embodiment, the switching element includes a diamagnetic material. In one embodiment, the switching element includes an antiferromagnetic material.

In one embodiment, the wearable absorbent hygiene article further includes a magnet fixed relative to the magnetic switch.

According to a second aspect, there is provided a system including the wearable absorbent hygiene article and the switching element according to the first aspect.

In one embodiment, the switching element is releasably attached to a surface of the wearable absorbent hygiene article. The magnetic switch is configured such that detaching the switching element from the surface switches the magnetic switch from the OFF state to the ON state.

As the switching element may be provided in a packaging in which the wearable absorbent hygiene article is packaged, unpacking of the wearable absorbent hygiene article may result in the switching of the magnetic switch. As the unpacking of a packaged wearable absorbent hygiene article may be an essential step for applying the wearable absorbent hygiene article, this configuration provides for reliable switching.

In embodiment, the switching element is provided in a pull-off tab.

With such a configuration, a convenient-to-use switching mechanism is provided. Specifically, a user may simply have to remove the pull-off tab when using the wearable absorbent hygiene article.

In one embodiment, the switching element is attachable to a surface of the wearable absorbent hygiene article. The magnetic switch is configured such that attaching the switching element to the surface switches the magnetic switch from the OFF state to the ON state.

With such a configuration, attachment of an entity including the switching element may be an essential step for applying the wearable absorbent hygiene article. This may provide for reliable switching.

In one embodiment, the switching element is provided in a tab.

With such a configuration, a convenient-to-use switching mechanism is provided. Specifically, a user may simply have to attach the tab when using the wearable absorbent hygiene article.

In a third aspect, there is provided a method of using a wearable absorbent hygiene article. The wearable absorbent hygiene article includes an electronics unit, a power source and a magnetic switch. The magnetic switch is configured such that the power source supplies power to the electronics unit when the magnetic switch is in an ON state and such that the power source does not supply power to the electronics unit when the magnetic switch is in an OFF state. The method includes the step of using the wearable absorbent hygiene article. In the using step, the magnetic switch is switched from the OFF state to the ON state due to a change in a magnetic field experienced by the magnetic switch.

Using the wearable absorbent hygiene article may include a change in the physical condition of the wearable absorbent hygiene article or a change in a physical condition surrounding the wearable absorbent hygiene article.

With such a method, it is possible to provide a convenient method of using a wearable absorbent hygiene article in which an electronics unit may be powered for a longer period of time when the wearable absorbent article is in use.

In one implementation, the step of using the wearable absorbent hygiene article includes the steps of: unpacking the wearable absorbent hygiene article from a packaging when the wearable absorbent hygiene article is packaged in the packaging; and/or unfolding the wearable absorbent hygiene article from a folded configuration of the wearable absorbent hygiene article; and/or applying the wearable absorbent hygiene article. In one of the unpacking, unfolding and applying steps, the magnetic switch is switched from the OFF state to the ON state due to a change in a magnetic field experienced by the magnetic switch.

Unpacking, unfolding and/or applying are typical steps in the use of conventional wearable absorbent hygiene articles. Accordingly, with such a method, the magnetic switch would automatically switch from the OFF state to the ON state during unpacking/unfolding/application of the wearable absorbent hygiene article, and, therefore, additional steps may not be required by the user to start powering the electronics unit.

In one implementation, the magnetic switch is switched from the OFF state to the ON state due to a relative movement between the magnetic switch and a switching element.

In one implementation, the wearable absorbent hygiene article prior to use is packaged in a packaging including a switching element. The step of using the wearable absorbent hygiene article includes the step of unpacking the wearable absorbent hygiene article. In the unpacking step, the magnetic switch is switched from the OFF state to the ON state due to a relative movement between the magnetic switch and the switching element.

In one implementation, prior to use, the wearable absorbent hygiene article is in a folded configuration. The step of using the wearable absorbent hygiene article includes the step of unfolding the wearable absorbent hygiene article. In the unfolding step, the magnetic switch is automatically switched from the OFF state to the ON state due to a relative movement between the magnetic switch and the switching element.

In one implementation, prior to use, the wearable absorbent hygiene article is packaged in a packaging. The step of using the wearable absorbent hygiene article includes the step of unpacking the wearable absorbent hygiene article. In the unpacking step, the magnetic switch is automatically switched from the OFF state to the ON state due to a relative movement between the magnetic switch and the switching element.

In one implementation, the step of using the wearable absorbent hygiene article includes the step of applying the wearable absorbent hygiene article. In the applying step, the magnetic switch is automatically switched from the OFF state to the ON state due to a relative movement between the magnetic switch and the switching element.

In one implementation, prior to use, the wearable absorbent hygiene article is in a folded configuration. Prior to use, the wearable absorbent hygiene article is packaged in a packaging. The step of using the wearable absorbent hygiene article includes the steps of: unpacking the wearable absorbent hygiene article; and unfolding the wearable absorbent hygiene article. In one of the unpacking and unfolding steps, the magnetic switch is automatically switched from the OFF state to the ON state due to a relative movement between the magnetic switch and the switching element.

In one implementation, prior to use, the wearable absorbent hygiene article is in a folded configuration. The step of using the wearable absorbent hygiene article includes the steps of: unfolding the wearable absorbent hygiene article; and applying the wearable absorbent hygiene article. In one of the unfolding and applying steps, the magnetic switch is automatically switched from the OFF state to the ON state due to a relative movement between the magnetic switch and the switching element.

In one implementation, prior to use, the wearable absorbent hygiene article is packaged in a packaging. The step of using the wearable absorbent hygiene article includes the steps of: unpacking the wearable absorbent hygiene article; and applying the wearable absorbent hygiene article. In one of the unpacking and applying steps, the magnetic switch is automatically switched from the OFF state to the ON state due to a relative movement between the magnetic switch and the switching element.

In one implementation, prior to use, the wearable absorbent hygiene article is in a folded configuration. Prior to use, the wearable absorbent hygiene article is packaged in a packaging. The step of using the wearable absorbent hygiene article includes the steps of: unpacking the wearable absorbent hygiene article; unfolding the wearable absorbent hygiene article; and applying the wearable absorbent hygiene article. In one of the unpacking, unfolding and applying steps, the magnetic switch is automatically switched from the OFF state to the ON state due to a relative movement between the magnetic switch and the switching element.

In one implementation, the switching element is releasably attachable to the wearable absorbent hygiene article. The relative movement between the magnetic switch and the switching element is due to detaching the switching element from the wearable absorbent hygiene article.

In one implementation, the switching element is attachable to the wearable absorbent hygiene article. The relative movement between the magnetic switch and the switching element is due to attaching the switching element to the wearable absorbent hygiene article.

In one implementation, the wearable absorbent hygiene article is the wearable absorbent hygiene article of the first aspect.

In one implementation, the wearable absorbent hygiene article is the wearable absorbent hygiene article of the system according to the second aspect. The switching element is the switching element of the system according to the second aspect.

In one implementation, the switching element includes a magnet.

In one implementation, the switching element includes a ferromagnetic material. In one implementation, the switching element includes a ferrimagnetic material. In one implementation, the switching element includes a paramagnetic material. In one implementation, the switching element includes a diamagnetic material. In one implementation, the switching element includes an antiferromagnetic material.

In one implementation, the wearable absorbent hygiene article further includes a magnet fixed relative to the magnetic switch.

Further features and effects of the wearable absorbent hygiene article and the method of using the wearable absorbent hygiene article of the disclosure will be evident from the following description of certain embodiments. In the description of these embodiments, reference is made to the accompanying drawings.

BRIEF DESCRIPTION OF THE DRAWINGS

For a better understanding of embodiments of the present invention and to show how the same may be carried into effect, reference will now be made, by way of example only, to the accompanying drawings, in which.

DETAILED DESCRIPTION PARTICULAR EMBODIMENTS

Figure 1:
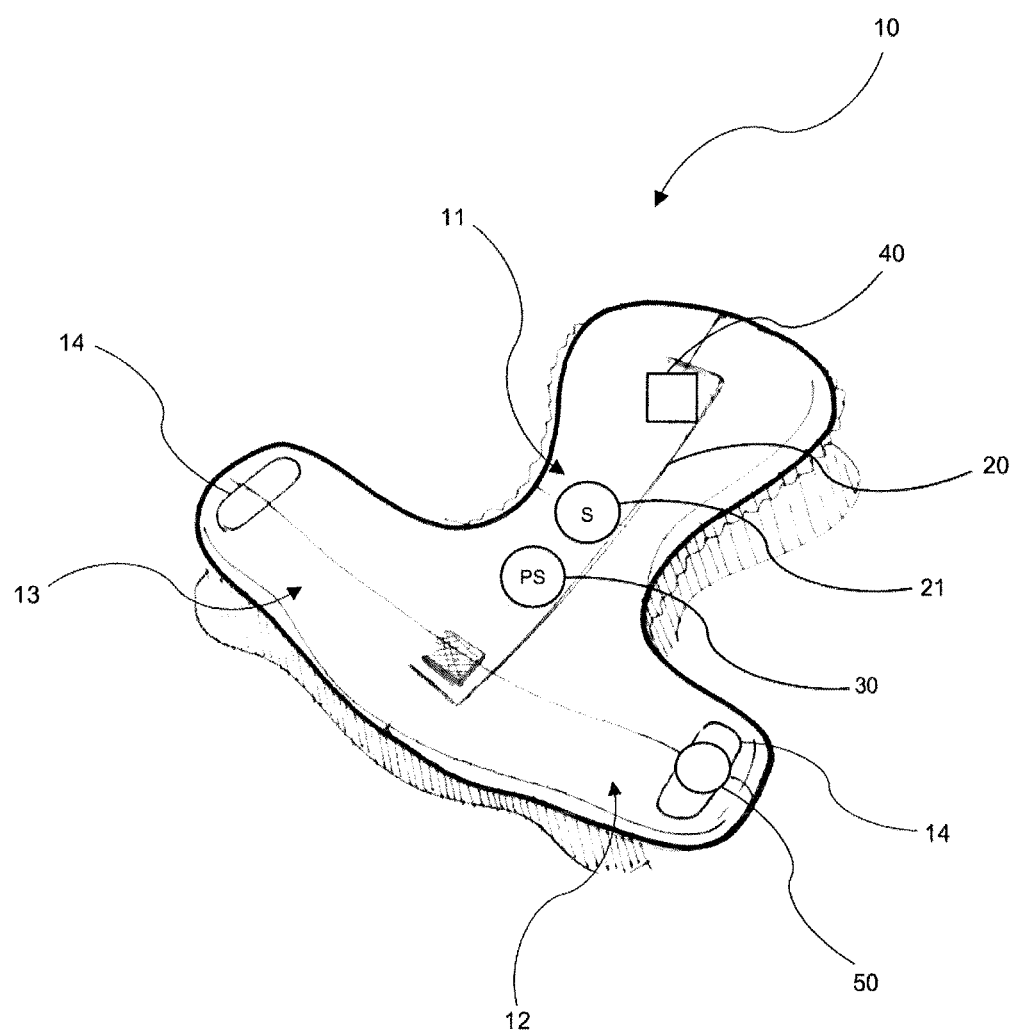
FIG. 1 shows a wearable absorbent hygiene article.

FIG. 1 shows a wearable absorbent hygiene article 10 according to a first embodiment.

In FIG. 1, the wearable absorbent hygiene article 10 has a main portion 11, a first side portion 12, a second side portion 13 and attachment members 14. The main portion 11 is elongate in a first direction. The first side portion 12 and the second side portion 13 extend away from the main portion 11 along a second direction perpendicular to the first direction. The first side portion 12 and the second side portion 13 extend away from the main portion 11 on opposite sides of the main portion 11. An attachment member 14 is disposed on both side portions 12, 13.

The wearable absorbent hygiene article 10 is configured to be worn around the waist of a user by attaching the side portions 12, 13 to the main portion 11 using the attachment members 14.

Figure 12:
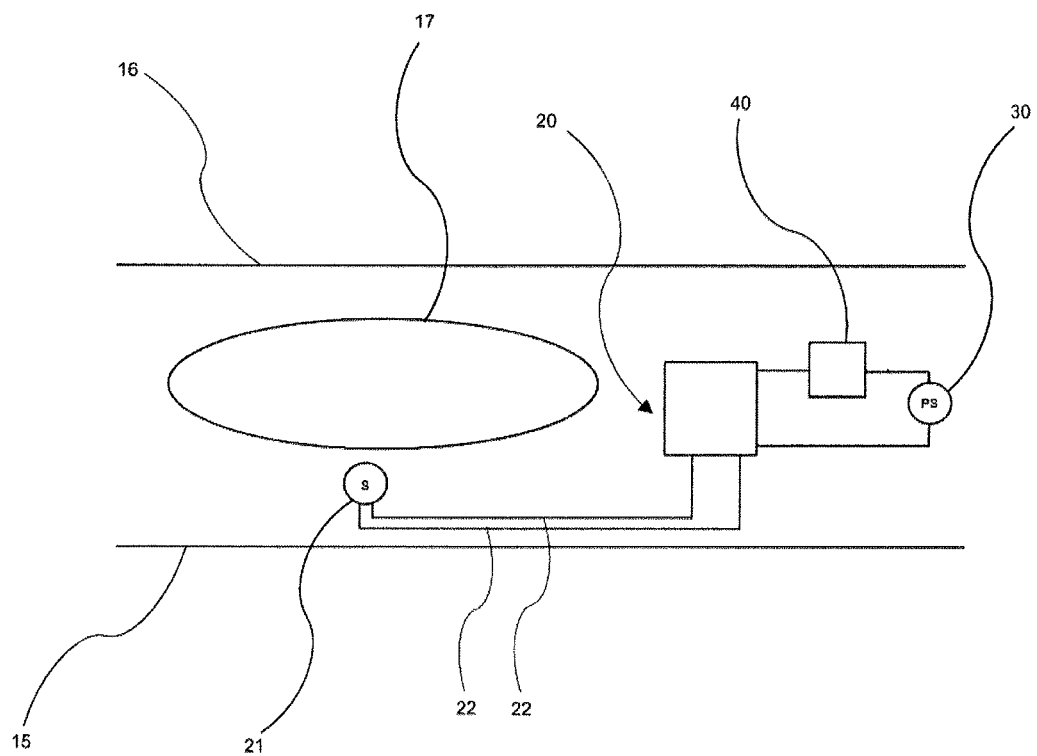
FIGS. 12 to 14 show various arrangements of the electronics unit, sensor, power source and switch of the wearable absorbent hygiene article.
Figure 13:
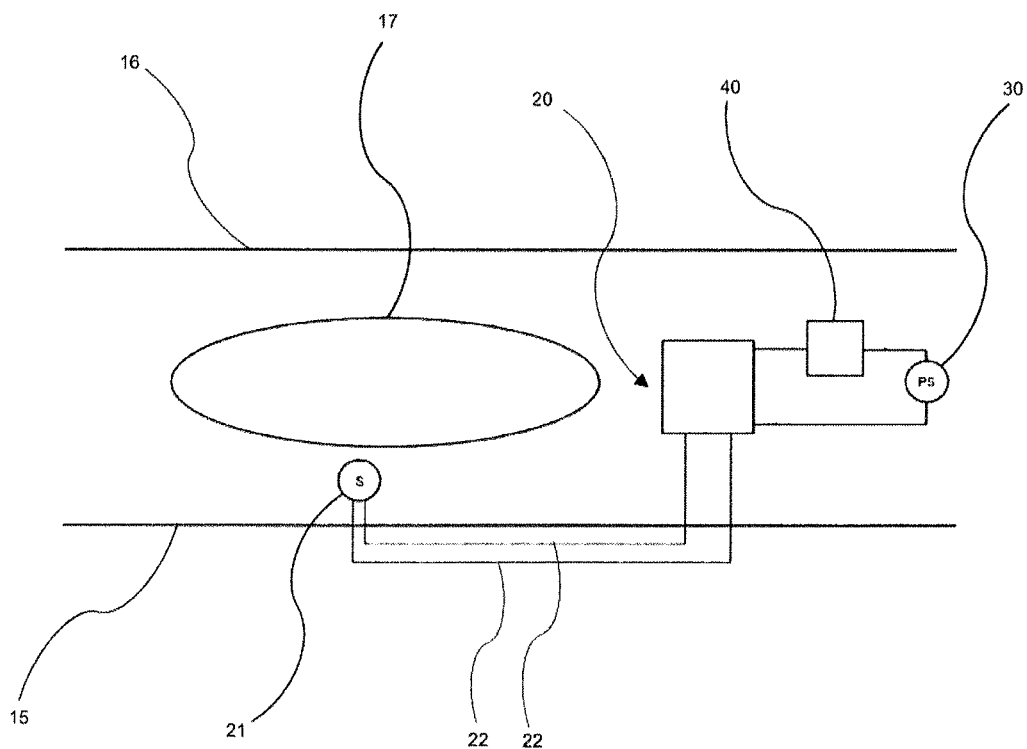
Figure 14:
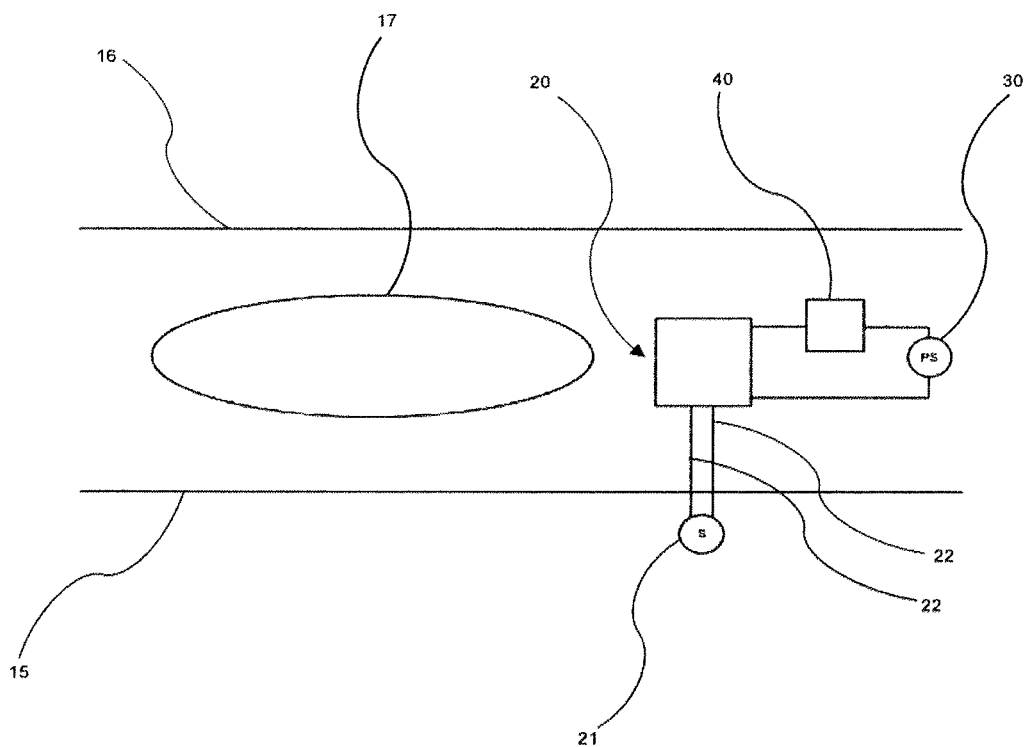

The wearable absorbent hygiene article 10 has a liquid permeable top layer adapted to face the wearer during use and adapted to allow a fluid such as urine or other bodily fluids to pass through; a liquid impermeable back layer adapted to face away from the wearer and adapted to prevent the fluid from passing through; and an absorbent member located between the top layer and the back layer (see FIGS. 12 to 14).

FIG. 1 shows the wearable absorbent hygiene article 10 in an unfolded configuration. This configuration of the wearable absorbent hygiene article 10 is typical before the application of the wearable absorbent hygiene article 10 to a wearer.

The wearable absorbent hygiene article 10 has an electronics unit 20. The electronics unit 20 is disposed in the main portion 11 of the wearable absorbent hygiene article 10. The electronics unit 20 may be configured to perform various tasks. For example, the electronics unit 20 may include a sensor 21 for sensing a physical environment present in the wearable absorbent hygiene article 10. The sensor may be a wetness sensor, a temperature sensor, a chemical sensor or a biological sensor. The electronics unit 20 may be configured in a variety of ways to perform a variety of different tasks.

The electronics unit 20 may further include a transmitter for transmitting information relating to the physical environment present in the wearable absorbent hygiene article 10 or other relevant information. The electronics unit 20 may further include a receiver for receiving information such as instructions.

The wearable absorbent hygiene article 10 includes a power source 30. In the wearable absorbent hygiene article 10 shown in FIG. 1, the power source 30 is provided in the main portion 11 of the wearable absorbent hygiene article 10. As shown, the power source 30 is disposed on the electronics unit 20. The power source 30 may hold an energy store in the form of electrical energy and/or a chemical energy. The power source 30 may be any type of power source such as a cell, battery and/or a capacitor. For example, the power source 30 may be a flexible paper cell/battery such as those provided by Blue Spark Technologies (OH, US), Enfucell Oy (FI), GS Nanotech (KR) or Cymbet (MN, US).

The wearable absorbent hygiene article 10 has a magnetic switch 40. In the wearable absorbent hygiene article 10 shown in FIG. 1, the magnetic switch 40 is provided in the main portion 11 of the wearable absorbent hygiene article 10. Accordingly, a movement/manipulation of the main portion 11 may result in a corresponding movement of the magnetic switch 40. As shown, the magnetic switch 40 is disposed on the electronics unit 20.

The magnetic switch 40 operably couples the electronics unit 20 to the power source 30. The magnetic switch 40 has an ON state and an OFF state. The magnetic switch 40 is configured such that the power source 30 supplies power to the electronics unit 20 when the magnetic switch 40 is in an ON state. The magnetic switch 40 is configured such that the power source 30 does not supply power to the electronics unit 20 when the magnetic switch 40 is in an OFF state. When the magnetic switch 40 is in the OFF state, a complete circuit between the power source 30 and the electronics unit 20 is not present. In such a state, the electronics unit 20 is not powered by the power source 30, and, therefore, the power source 30 largely maintains its energy store.

The wearable absorbent article 10 has a switching element 50. In the wearable absorbent hygiene article 10 shown in FIG. 1, the switching element 50 is disposed in the first side portion 12 of the wearable absorbent hygiene article 10. Accordingly, a movement/manipulation of the first side portion 12 may result in a corresponding movement of the switching element 50.

The magnetic switch 40 is configured such that a movement of the switching element 50 relative to the magnetic switch 40 switches the magnetic switch 40 from the OFF state to the ON state. The movement of the switching element 50 relative to magnetic switch 40 is a predetermined movement which will be detailed with respect to FIGS. 2 and 3. This predetermined movement of the switching element 50 relative to the magnetic switch 40 causes a change in the magnetic field experienced by the magnetic switch 40. The magnetic switch 40 is configured such that this particular change in magnetic field causes the magnetic switch 40 to switch from the OFF state to the ON state.

In the remaining figures, the sensor 21 and/or the power source 30 may not be shown for simplicity.

Figure 2:
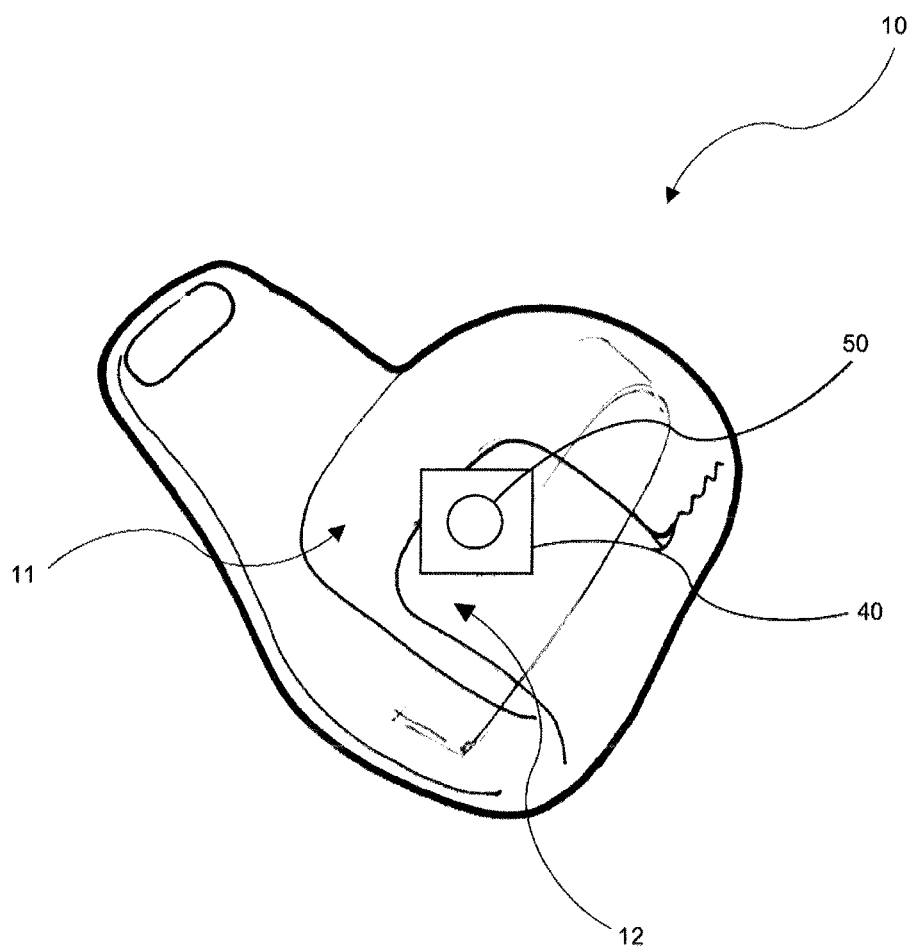
FIG. 2 shows the wearable absorbent hygiene article of FIG. 1 in a part-folded configuration.

FIG. 2 shows the wearable absorbent hygiene article 10 of the first embodiment in a part-folded configuration.

In this configuration, the main portion 11 is folded such that regions of the main portion 11 overlap with each other. Furthermore, the first side portion 12 is folded over the main portion 11 such that a region of the first side portion 12 overlaps with a region of the main portion 11. In this configuration, the switching element 50 disposed in the first side portion 12 is in close proximity with the magnetic switch 40 disposed in the main portion 11. Specially, the switching element 50 may overlap with the magnetic switch 40. Hence, in this configuration, the magnetic switch 50 experiences a first magnetic field.

Figure 3:
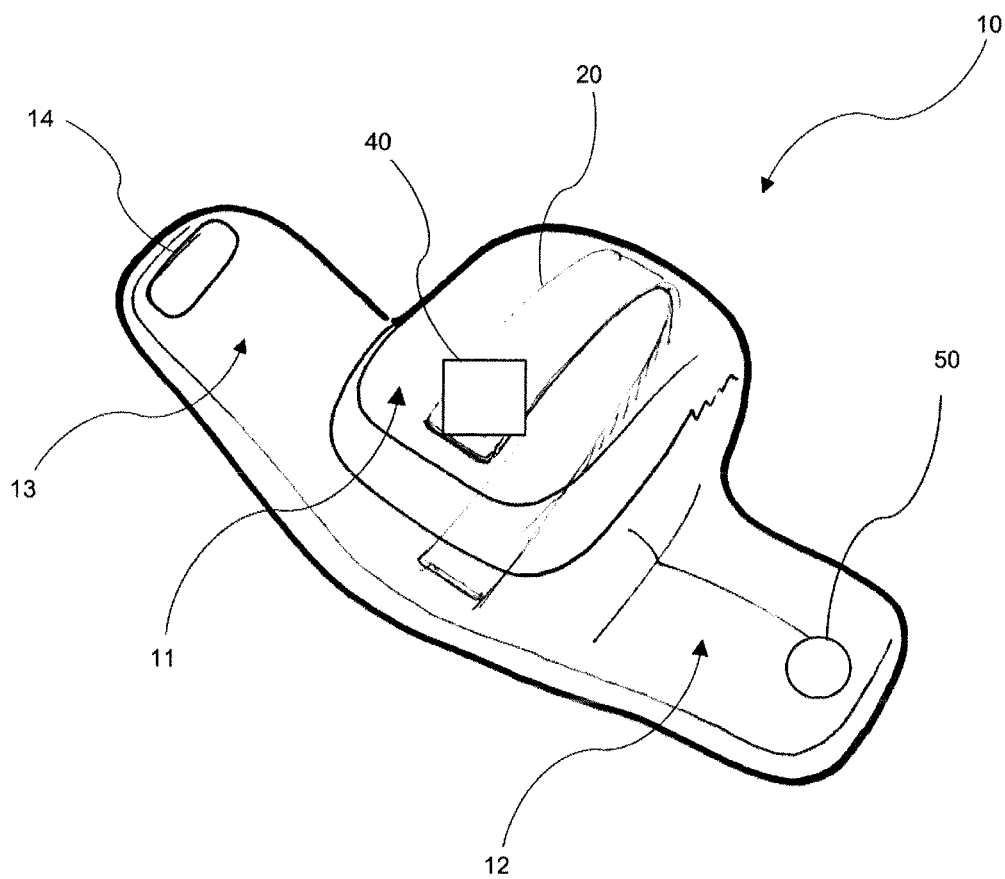
FIG. 3 shows the wearable absorbent hygiene article of FIG. 1 in a part-unfolded configuration.

FIG. 3 shows the wearable absorbent hygiene article 10 of the first embodiment in a part-unfolded configuration. This configuration may result from a user partly unfolding the wearable absorbent hygiene article 10 from the configuration shown in FIG. 2. Specifically, in FIG. 3, the first side portion 12 has been unfolded away from the main portion 11 as compared with the configuration shown in FIG. 2. In doing so, the switching element 50 has been moved away from the magnetic switch 40. Hence, in this configuration, the magnetic switch 40 experiences a second magnetic field. Specifically, the magnetic field experienced by the magnetic switch 40 in the configuration shown in FIG. 3 may be smaller than the magnetic field experienced by the magnetic switch 40 in the configuration shown in FIG. 2. The magnetic switch 40 may be configured such that this change in magnetic field experienced by the magnetic switch 40 switches the magnetic switch 40 from the OFF state to the ON state. Accordingly, the magnetic switch 40 is configured to switch from the OFF state to the ON state when the user unfolds the first side portion 12 of the wearable absorbent hygiene article 10 from the folded configuration shown in FIG. 2 to the unfolded configuration shown in FIG. 3.

A method of using the wearable absorbent hygiene article 10 of the first embodiment will now be described with respect to FIGS. 2 and 3. Generally, using the wearable absorbent hygiene article 10 may include a change in the physical condition of the wearable absorbent hygiene article 10 or a change in a physical condition surrounding the wearable absorbent hygiene article 10. In particular, using the wearable absorbent hygiene article 10 of the first embodiment includes unfolding the wearable absorbent hygiene article 10 from the folded configuration shown in FIG. 2 to the partly-unfolded configuration shown in FIG. 3. Before this unfolding step, the magnetic switch is in the OFF state. During the unfolding step, the magnetic switch 40 is switched from the OFF state to the ON state such that the electronics unit 20 is powered by the power source 30. Once the wearable absorbent hygiene article 10 is completely unfolded as in the configuration shown in FIG. 1, it may then be applied to the waist of the wearer.

Figure 4:
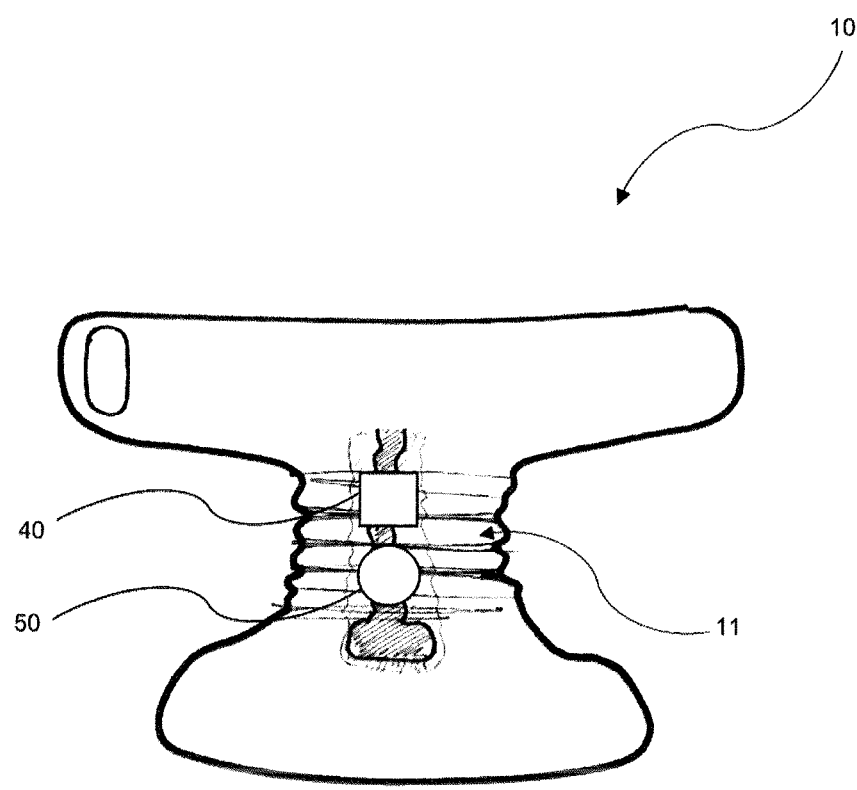
FIG. 4 shows another embodiment of the wearable absorbent hygiene article in a contracted configuration.

FIG. 4 shows a second embodiment of the wearable absorbent hygiene article 10. The wearable absorbent hygiene article 10 of the second embodiment is generally similar to the wearable absorbent hygiene article 10 of the first embodiment. Accordingly, only certain differences of the second embodiment will be described below.

FIG. 4 shows the wearable absorbent hygiene article 10 in a contracted configuration.

In this contracted configuration, the main portion 11 of the wearable absorbent hygiene article 10 is contracted along the first direction. In this configuration, the magnetic switch 40 and the switching element 50 are disposed in close proximity to one another. Hence, in this configuration, the magnetic switch 50 experiences a first magnetic field.

Figure 5:
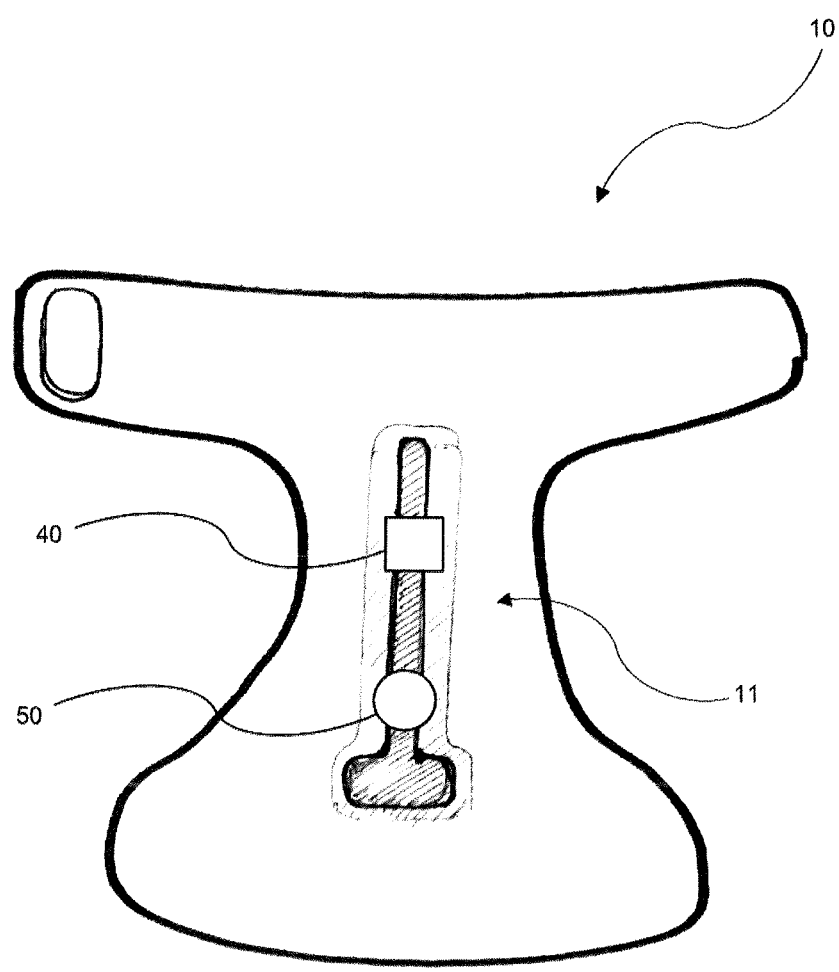
FIG. 5 shows the wearable absorbent hygiene article of FIG. 4 in an expanded configuration.

FIG. 5 shows the wearable absorbent hygiene article 10 of the second embodiment in an expanded configuration. This configuration may result from a user expanding the main portion 11 along the first direction of the wearable absorbent hygiene article 10 from the configuration shown in FIG. 4. In doing so, the switching element 50 has been moved away from the magnetic switch 40. Hence, in this configuration, the magnetic switch 40 experiences a second magnetic field. Specifically, the magnetic field experienced by the magnetic switch 40 in the configuration shown in FIG. 5 may be smaller than the magnetic field experienced by the magnetic switch 40 in the configuration shown in FIG. 4. The magnetic switch 40 may be configured such that this change in magnetic field experienced by the magnetic switch 40 switches the magnetic switch 40 from the OFF state to the ON state. Accordingly, the magnetic switch 40 is configured to switch from the OFF state to the ON state when the user expands the main portion 11 of the wearable absorbent hygiene article 10 from the contracted configuration shown in FIG. 4 to the expanded configuration shown in FIG. 5.

A method of using the wearable absorbent hygiene article 10 of the second embodiment will now be described with respect to FIGS. 4 and 5. Using the wearable absorbent hygiene article 10 of the second embodiment includes expanding the wearable absorbent hygiene article 10 from the contracted configuration shown in FIG. 4 to the expanded configuration shown in FIG. 5. Before this expanding step, the magnetic switch is in the OFF state. During the expanding step, the magnetic switch 40 is switched from the OFF state to the ON state such that the electronics unit 20 is powered by the power source 30. Once the wearable absorbent hygiene article 10 is expanded, it may then be applied to the waist of the wearer.

Figure 6:
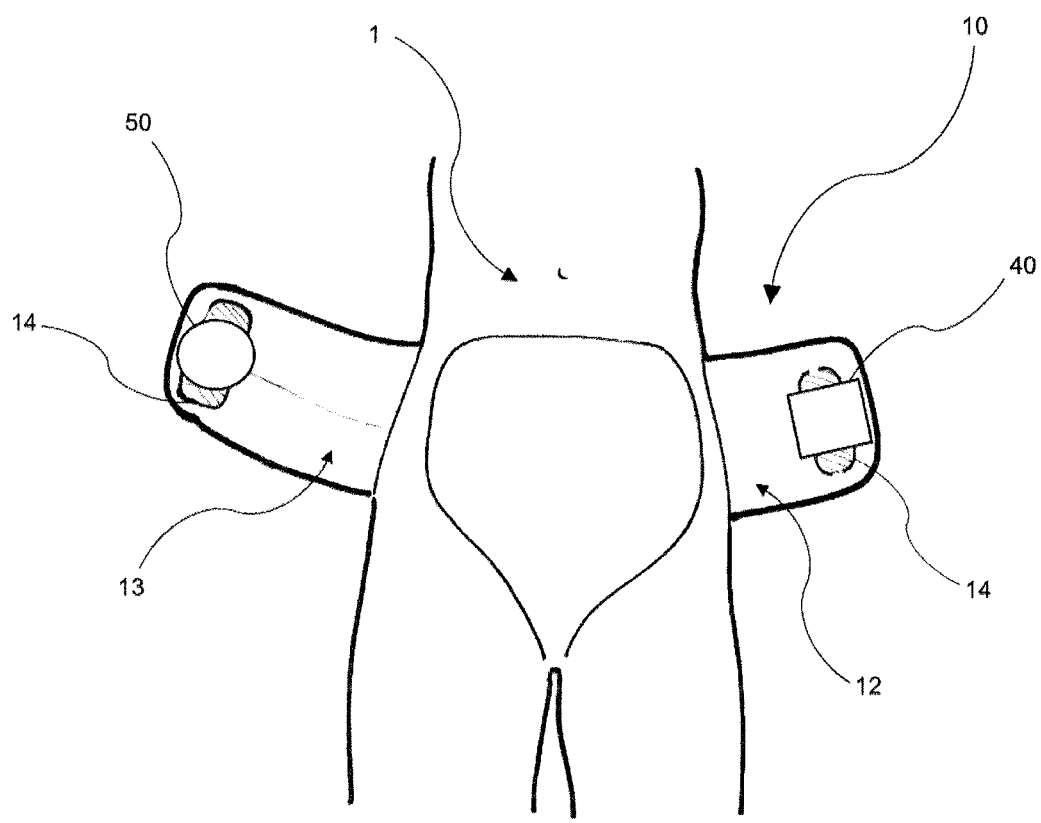
FIG. 6 shows another wearable absorbent article in an open configuration.

FIG. 6 shows a third embodiment of the wearable absorbent hygiene article 10. The wearable absorbent hygiene article 10 of the third embodiment is generally similar to the wearable absorbent hygiene article 10 of the previous embodiments. Accordingly, only certain differences of the third embodiment will be described below.

FIG. 6 shows the wearable absorbent hygiene article 10 in an open configuration before being applied to the waist of a user 1.

The first side portion 12 has a magnetic switch. The second side portion 13 has a switching element 50. The first side portion 12 and the second side portion 13 each have an attachment member 14. In the open configuration shown, the first side portion 12 and the second side portion 13 are separated from one another. As the magnetic switch 40 and the switching element 50 are disposed relatively distally from one another, in this configuration, the magnetic switch 40 experiences a first magnetic field.

Figure 7:
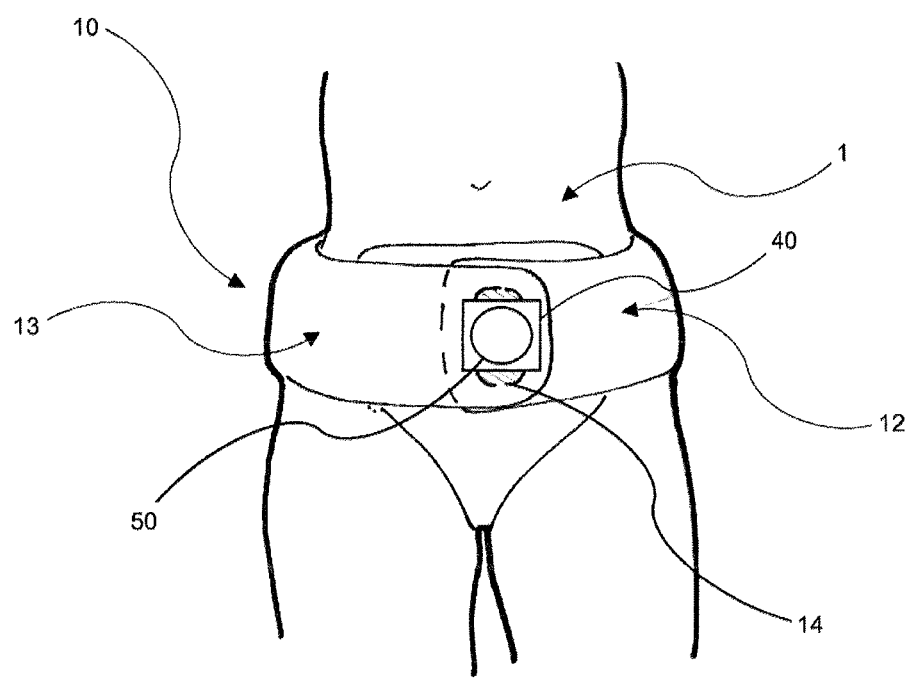
FIG. 7 shows the wearable absorbent article of FIG. 6 in a closed configuration.

FIG. 7 shows the wearable absorbent hygiene article 10 of the third embodiment in a closed configuration in which the wearable absorbent hygiene article 10 has been applied to the waist of a user 1. This configuration may result from a user bringing the first side portion 12 and the second side portion 13 into contact with one another from the configuration shown in FIG. 6. In doing so, the user may have attached the attachment members 14 of the first side portion 12 and the second side portion 13 to each other, thereby securing the wearable absorbent hygiene article 10 to the waist of the user 1. Bringing together the first side portion 12 and the second side portion 13 results in the switching element 50 being moved towards the magnetic switch 40. As shown in FIG. 7, in the closed configuration, the magnetic switch 40 and the switching element 50 overlap with one another. In this configuration, the magnetic switch 40 experiences a second magnetic field. Specifically, the magnetic field experienced by the magnetic switch 40 in the closed configuration shown in FIG. 7 may be larger than the magnetic field experienced by the magnetic switch 40 in the open configuration shown in FIG. 6. The magnetic switch 40 may be configured such that this change in magnetic field experienced by the magnetic switch 40 switches the magnetic switch 40 from the OFF state to the ON state. Accordingly, the magnetic switch 40 is configured to switch from the OFF state to the ON state when the user brings the first side portion 12 and the second side portion 13 together when applying the wearable absorbent hygiene article 10 from the open configuration shown in FIG. 6 to the closed configuration shown in FIG. 7.

A method of using the wearable absorbent hygiene article 10 of the third embodiment will now be described with respect to FIGS. 6 and 7. Using the wearable absorbent hygiene article 10 of the third embodiment includes applying the wearable absorbent hygiene article 10 to a user 1. Applying the wearable absorbent hygiene article 10 includes bringing the first side portion 12 and the second side portion 13 into contact with each other such that the attachment members 14 on each of the side portions 12, 13 attach to each other. This can be effected from the open configuration shown in FIG. 6 so as to result in the closed configuration shown in FIG. 7. Before this applying step, the magnetic switch 40 is in the OFF state. During the applying step, the magnetic switch 40 is switched from the OFF state to the ON state such that the electronics unit 20 (not shown in FIGS. 6 and 7) is powered by the power source 30 (not shown in FIGS. 6 and 7).

Figure 8:
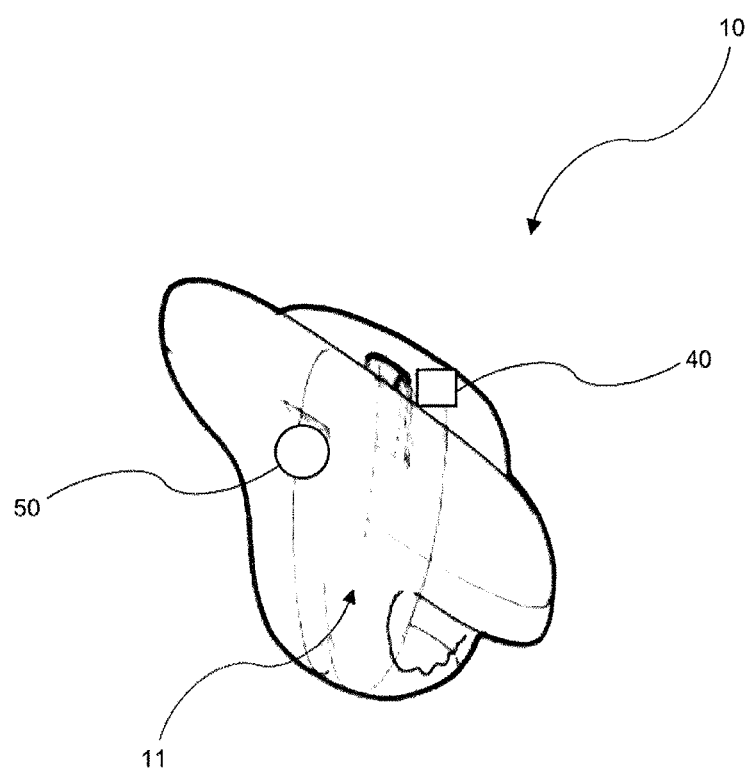
FIG. 8 shows another wearable absorbent article in a folded configuration.

FIG. 8 shows a fourth embodiment of the wearable absorbent hygiene article 10. The fourth embodiment is generally similar to the wearable absorbent hygiene article 10 of the previous embodiments. Accordingly, only certain differences of the fourth embodiment will be described below.

FIG. 8 shows the wearable absorbent hygiene article 10 in a folded configuration.

In this folded configuration, the main portion 11 of the wearable absorbent hygiene article 10 is folded. In this configuration, the magnetic switch 40 and the switching element 50 are disposed in close proximity to one another. Hence, in this configuration, the magnetic switch 50 experiences a first magnetic field.

Figure 9:
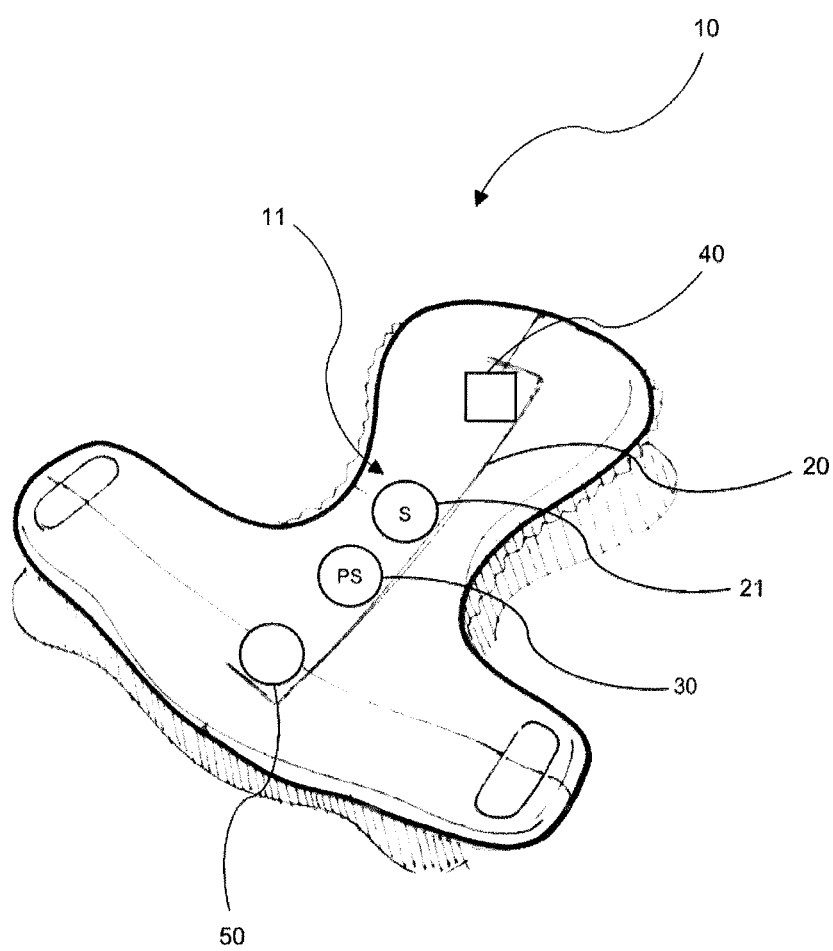
FIG. 9 shows the wearable absorbent article of FIG. 8 in an unfolded configuration.

FIG. 9 shows the wearable absorbent hygiene article 10 of the fourth embodiment in an unfolded configuration. This configuration may result from a user unfolding the main portion 11 of the wearable absorbent hygiene article 10 from the configuration shown in FIG. 8. In doing so, the switching element 50 has been moved away from the magnetic switch 40. Hence, in this configuration, the magnetic switch 40 experiences a second magnetic field. Specifically, the magnetic field experienced by the magnetic switch 40 in the configuration shown in FIG. 9 may be smaller than the magnetic field experienced by the magnetic switch 40 in the configuration shown in FIG. 8. The magnetic switch 40 may be configured such that this change in magnetic field experienced by the magnetic switch 40 switches the magnetic switch 40 from the OFF state to the ON state. Accordingly, the magnetic switch 40 is configured to switch from the OFF state to the ON state when the user unfolds the main portion 11 of the wearable absorbent hygiene article 10 from the folded configuration shown in FIG. 8 to the unfolded configuration shown in FIG. 9.

A method of using the wearable absorbent hygiene article 10 of the fourth embodiment will now be described with respect to FIGS. 8 and 9. Using the wearable absorbent hygiene article 10 of the fourth embodiment includes unfolding the wearable absorbent hygiene article 10 from the folded configuration shown in FIG. 8 to the unfolded configuration shown in FIG. 9. Before this unfolding step, the magnetic switch is in the OFF state. During the unfolding step, the magnetic switch is switched from the OFF state to the ON state such that the electronics unit 20 (not shown in FIG. 8) is powered by the power source 30 (not shown in FIG. 8). Once the wearable absorbent hygiene article is unfolded, it may then be applied to the waist of the wearer.

Figure 10:
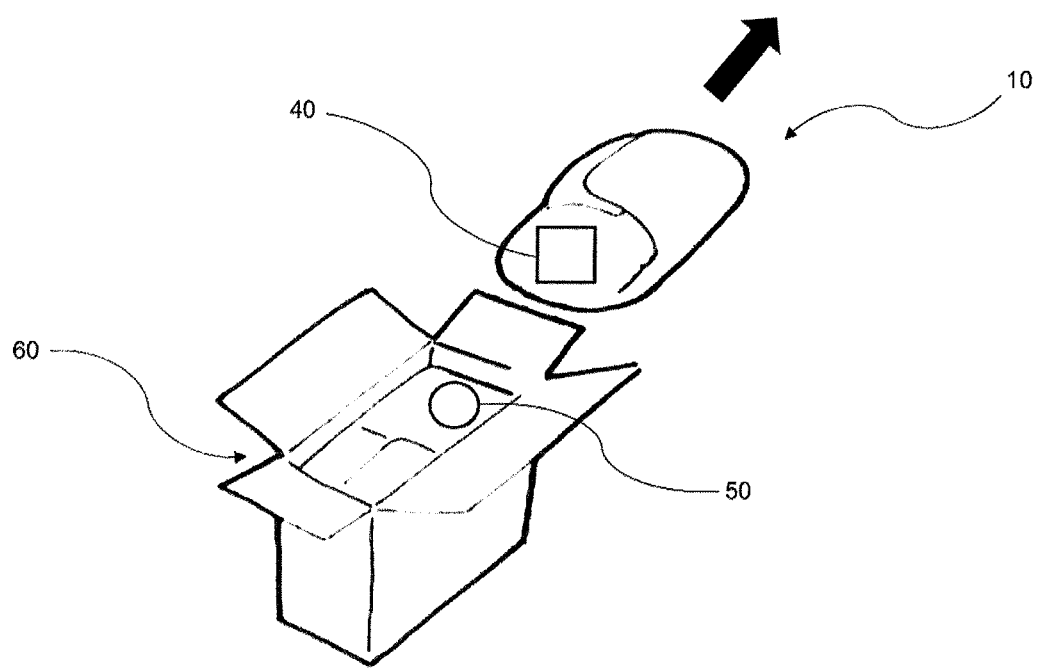
FIG. 10 shows another wearable absorbent article.

FIG. 10 shows a fifth embodiment of the wearable absorbent hygiene article 10. The wearable absorbent hygiene article 10 of the fifth embodiment is generally similar to the wearable absorbent hygiene article 10 of the previous embodiments. Accordingly, only certain differences of the fifth embodiment will be described below.

The wearable absorbent hygiene article 10 of the fifth embodiment does not have a switching element 50. Instead, the magnetic switch 40 is switched from the OFF state to the ON state due to a relative movement between the magnetic switch 40 and a switching element 50 which is provided on a packaging box 60.

FIG. 10 shows the wearable absorbent hygiene article 10 being unpacked from the packaging box 60 by movement in the direction shown by the arrow. Previous to this state, the magnetic switch 40 and the switching element 50 disposed in the packaging box 60 are in close proximity to one another. Hence, in a state prior to this configuration, the magnetic switch 50 experiences a first magnetic field.

As the wearable absorbent hygiene article 10 is moved away from the packaging box 60 and the switching element 50, the magnetic field experienced by the magnetic switch 40 may decrease. The magnetic switch 40 may be configured such that this change in magnetic field experienced by the magnetic switch 40 switches the magnetic switch from the OFF state to the ON state. Accordingly, the magnetic switch 40 is configured to switch from the OFF state to the ON state when the user unpacks the wearable absorbent hygiene article 10 from the packaging box 60.

A method of using the wearable absorbent hygiene article 10 of the fifth embodiment will now be described with respect to FIG. 10. Using the wearable absorbent hygiene article 10 of the fifth embodiment includes unpacking the wearable absorbent hygiene article 10 from the packaging box 60. Unpacking the wearable absorbent hygiene article 10 from the packaging box 60 includes moving the wearable absorbent hygiene article 10 away from packaging box 60, as shown by the arrow in FIG. 10. Before this unpacking step, the magnetic switch is in the OFF state. During the unpacking step, the magnetic switch 40 is switched from the OFF state to the ON state such that the electronics unit 20 (not shown in FIG. 10) is powered by the power source 30 (not shown in FIG. 10). Once the wearable absorbent hygiene article 10 is unpackaged, it may then be applied to the waist of the wearer.

Figure 11:
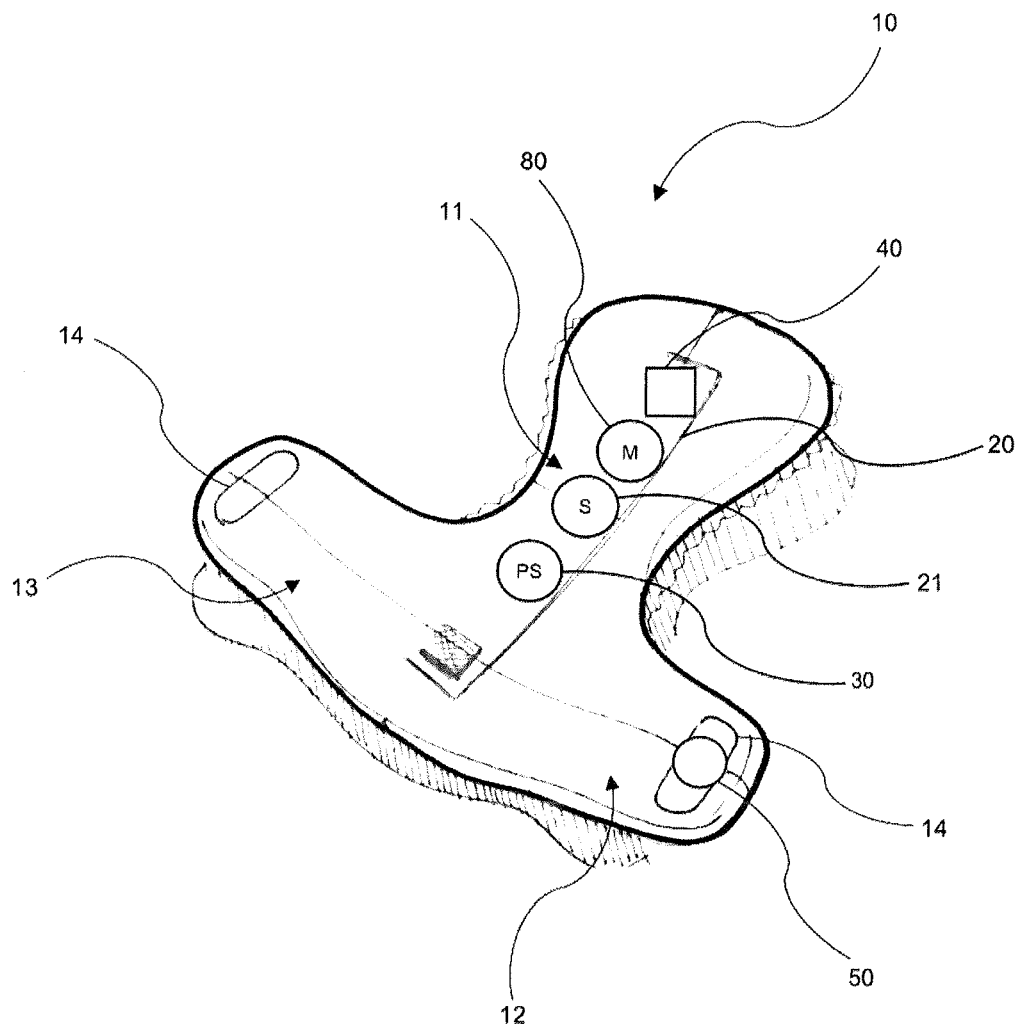
FIG. 11 shows another wearable absorbent hygiene article.

FIG. 11 shows a sixth embodiment of the wearable absorbent hygiene article 10. The sixth embodiment is generally similar to the wearable absorbent hygiene article 10 of the previous embodiments. Accordingly, only certain differences of the sixth embodiment will be described below.

FIG. 11 shows the wearable absorbent hygiene article 10 in an unfolded configuration. The wearable absorbent hygiene article 10 has a magnet 80 fixed relative to the magnetic switch 40. Accordingly, no relative movement between the magnetic switch 40 and the magnet 80 occurs or any (small) relative movement between the magnetic switch 40 and the magnet 80 does not switch the magnetic switch 40 from the OFF state to the ON state.

The wearable absorbent hygiene article 10 has a switching element 50. In the wearable absorbent hygiene article 10 shown in FIG. 11, the switching element 50 is disposed in the first side portion 12 of the wearable absorbent hygiene article 10. Accordingly, a movement/manipulation of the first side portion 12 may result in a corresponding movement of the switching element 50.

In this embodiment, the switching element 50 includes a ferromagnetic material.

Movement of the switching element 50 closer to the magnetic switch 40 may enhance the magnetic field experienced by the magnetic switch 40 caused by the magnet 80. In this embodiment, the magnetic switch 40 is configured such that a movement of the switching element 50 including a ferromagnetic material relative to the magnetic switch 40 switches the magnetic switch 40 from the OFF state to the ON state. The movement of the switching element 50 relative to the magnetic switch 40 is a predetermined movement which may be similar to the movements described with respect to FIGS. 2 and 3.

FIGS. 12, 13 and 14 show various arrangements of the electronics unit 20, sensor 21, power source 30 and switch 40 of the wearable absorbent hygiene article 10. In each of these embodiments, the wearable absorbent hygiene article 10 has a top layer 15 adapted to face the wearer during use, a back layer 16 opposite to the top layer 15, and an absorbent member 17 located between the back layer 15 and the top layer 16. FIGS. 12, 13 and 14 show a cross-section of a portion of the wearable absorbent hygiene article 10. For example, these cross-sections may be cross-sections of the main portion 11 of the wearable absorbent hygiene article 10.

FIG. 12 shows an embodiment in which the power source 30, the magnetic switch 40 and the whole of the electronics unit 20, including the sensor 21, are disposed between the back layer 15 and the top layer 16.

FIG. 13 shows an alternate embodiment in which the leads 22 of the electronics unit 20 are not disposed between the back layer 15 and the top layer 16. Accordingly, only a portion of the electronics unit 20 is disposed between the top layer 16 and the back layer 15.

FIG. 14 shows another embodiment in which the sensor 21 of the electronics unit 20 is not disposed between the back layer 15 and the top layer 16. Accordingly, only a portion of the electronics unit 20 is disposed between the back layer 15 and the top layer 16.

In the various embodiments described in this disclosure, and in particular the embodiments described with respect to FIGS. 1 to 10, the switching element 50 may include a magnet.

In the various embodiments described in this disclosure, and in particular the embodiments described with respect to FIG. 12, the switching element 50 may include a ferromagnetic material, a ferrimagnetic material, a paramagnetic material, a diamagnetic material, or an antiferromagnetic material.

Although the above explanation is considered to fully clarify how embodiments of the present invention may straightforwardly be put into effect by those skilled in the art, it is to be regarded as purely exemplary.

In particular, there are a number of variations which are possible, as may be appreciated by those skilled in the art.

For example, the magnetic switch 40 and the switching element 50 may be disposed in various locations within the wearable absorbent hygiene article 10 as long as the magnetic switch 40 is configured such that a movement of the switching element 50 relative to the magnetic switch 40 switches the magnetic switch 40 from the OFF state to the ON state.

For example, the movement that switches the magnetic switch 40 from the OFF state to the ON state may be any movement that occurs during the use of the wearable absorbent hygiene article 10. The use of the wearable absorbent hygiene article 10 includes unpacking the wearable absorbent hygiene article 10 from a packaging; unfolding the wearable absorbent hygiene article 10 from a folded configuration of the wearable absorbent hygiene article 10; and applying the wearable absorbent hygiene article 10 to a user.

In an alternative to the second embodiment shown in FIGS. 4 and 5, the wearable absorbent hygiene article 10 may be contracted in any portion of the wearable absorbent hygiene article 10. For example, the wearable absorbent hygiene article 10 may be contracted along the first side portion 12 and/or the second side portion 13. In such configurations, the magnetic switch 40 and the switching element 50 may be disposed along these contracted portions such that expanding these contracted portions results in the magnetic switch 40 and the switching element 50 being moved away from each other.

Furthermore, in the third embodiment shown in FIGS. 6 and 7, the first side portion 12 and the second side portion 13 may be side flaps or belt flaps.

In an alternative to the fifth embodiment shown in FIG. 10, the wearable absorbent hygiene article 10 may be initially packaged in a packaging bag which includes a switching element 50. In unpacking the wearable absorbent hygiene article 10 during use, the wearable absorbent hygiene article 10 is removed from the packaging bag such that the magnetic switch 40 and the switching element 50 are moved away from one another. This movement of the magnetic switch 40 and the switching element 50 may result in the magnetic switch 40 switching from the OFF state to the ON state.

The switching element 50 may be present in any external entity such that during use of the wearable absorbent hygiene article 10, there is a relative movement between the magnetic switch 40 and the switching element 50. For example, the switching element 50 may be provided on a tab which, prior to use, is fixed to the wearable absorbent hygiene article 10 such that when using the wearable absorbent hygiene article 10, the user must remove the tab such that the switching element 50 is moved away from the magnetic switch 40. This movement may result in the magnetic switch 40 being switched from the OFF state to the ON state. In another embodiment, the switching element 50 may be provided on a tab which is to be attached to the wearable absorbent hygiene article 10 during use such that this attachment results in the switching element 50 being moved closer to magnetic switch 40. This movement may result in the magnetic switch 40 being switched from the OFF state to the ON state.

In alternative embodiments to the embodiments shown in FIGS. 12, 13 and 14, the power source 30 may not be disposed between the back layer 15 and the top layer 16 and/or the magnetic switch 40 may not be disposed between the back layer 15 and the top layer 16.

All of the above are fully within the scope of the present invention, and are considered to form the basis for alternative embodiments in which one or more combinations of the above-described features are applied, without limitation to the specific combinations disclosed above.

In light of this, there will be many alternatives which implement the teaching of the present invention. It is expected that one skilled in the art will be able to modify and adapt the above disclosure to suit its own circumstances and requirements within the scope of the present invention, while retaining some or all technical effects of the same, either disclosed or derivable from the above, in light of his general knowledge in this art. All such equivalents, modifications or adaptations fall within the scope of the invention hereby defined by the claims.

The invention claimed is:

1. A wearable absorbent hygiene article comprising:
   an electronics unit;
   a power source; and
   a magnetic switch operably coupling the electronics unit to the power source, the magnetic switch configured such that the power source supplies power to the electronics unit when the magnetic switch is in an ON state and such that the power source does not supply power to the electronics unit when the magnetic switch is in an OFF state,
   wherein the magnetic switch is configured such that a change in a magnetic field experienced by the magnetic switch switches the magnetic switch from the OFF state to the ON state.

2. The wearable absorbent hygiene article of claim 1, wherein the magnetic switch is a reed switch.

3. The wearable absorbent hygiene article of claim 1, wherein the magnetic switch is configured such that a movement of a switching element relative to the magnetic switch switches the magnetic switch from the OFF state to the ON state.

4. The wearable absorbent hygiene article of claim 3, wherein the wearable absorbent hygiene article further comprises the switching element.

5. The wearable absorbent hygiene article of claim 4, wherein the wearable absorbent hygiene article comprises a first region and a second region, and wherein the magnetic switch is disposed in the first region and the switching element is disposed in the second region or the switching element is disposed in the first region and the magnetic switch is disposed in the second region.

6. The wearable absorbent hygiene article of claim 5, wherein the wearable absorbent hygiene article comprises a main portion, and wherein the first region is one region of the main portion and the second region is another region of the main portion.

7. The wearable absorbent hygiene article of claim 6, wherein, in a contracted configuration, the main portion is contracted such that the first region and the second region are in closer proximity to each other than in an expanded configuration of the wearable absorbent hygiene article.

8. The wearable absorbent hygiene article of claim 5, wherein, in a folded configuration, the wearable absorbent hygiene article is folded such that the first region and the second region at least partially overlap.

9. The wearable absorbent hygiene article of claim 5, wherein the first region and the second region are releasably attachable to each other.

10. The wearable absorbent hygiene article of claim 9, wherein the magnetic switch is configured such that attaching the first region and the second region to each other switches the magnetic switch from the OFF state to the ON state.

11. The wearable absorbent hygiene article of claim 9, wherein at least one of the first region and the second region is a side flap or a belt flap.

12. The wearable absorbent hygiene article of claim 5, wherein the first region is a main portion and the second region is a side portion of the wearable absorbent hygiene article.

13. The wearable absorbent hygiene article of claim 12, wherein, in a folded configuration, the wearable absorbent hygiene article is folded such that the main portion and the side portion at least partially overlap.

14. The wearable absorbent hygiene article of claim 4, wherein the magnetic switch is configured such that a bending, stretching, or compressing of a portion of the wearable absorbent hygiene article switches the magnetic switch from the OFF state to the ON state.

15. The wearable absorbent hygiene article of claim 3, wherein the switching element comprises a magnet.

16. The wearable absorbent hygiene article of claim 3, wherein the switching element comprises a ferromagnetic material, a ferrimagnetic material, paramagnetic material, diamagnetic material, or antiferromagnetic material.

17. The wearable absorbent hygiene article of claim 16, further comprising a magnet fixed relative to the magnetic switch.

18. The wearable absorbent hygiene article of claim 1, wherein the electronics unit comprises at least one sensor for sensing a physical environment present in the wearable absorbent hygiene article.

19. The wearable absorbent hygiene article of claim 1, wherein the electronics unit comprises a transmitter, a receiver, or both.

20. The wearable absorbent hygiene article of claim 1, wherein the power source is a cell.

21. The wearable absorbent hygiene article of claim 1, further comprising:
    a liquid permeable top layer adapted to face the wearer during use;
    a back layer opposite the top layer; and
    an absorbent member located between the top layer and the back layer, wherein:
    at least the power source, the magnetic switch, and at least a portion of the electronics unit are disposed between the top layer and the back layer.

22. The wearable absorbent hygiene article of claim 21, wherein the switching element is disposed between the top layer and the back layer.

* * * * *